United States Patent
Cohen et al.

(10) Patent No.: US 10,857,162 B2
(45) Date of Patent: *Dec. 8, 2020

(54) COMPOSITIONS FOR IMPROVING CELL VIABILITY AND METHODS OF USE THEREOF

(71) Applicant: Amylyx Pharmaceuticals Inc., Cambridge, MA (US)

(72) Inventors: Joshua Cohen, Canton, MA (US); Justin Klee, Cambridge, MA (US)

(73) Assignee: Amylyx Pharmaceuticals Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/781,239

(22) Filed: Feb. 4, 2020

(65) Prior Publication Data

US 2020/0171052 A1 Jun. 4, 2020

Related U.S. Application Data

(63) Continuation of application No. 16/280,861, filed on Feb. 20, 2019, which is a continuation of application No. 15/837,866, filed on Dec. 11, 2017, now Pat. No. 10,251,896, which is a continuation of application No. 14/140,083, filed on Dec. 24, 2013, now Pat. No. 9,872,865.

(60) Provisional application No. 61/804,690, filed on Mar. 24, 2013.

(51) Int. Cl.
*A61K 31/192* (2006.01)
*A61K 31/575* (2006.01)

(52) U.S. Cl.
CPC .......... *A61K 31/575* (2013.01); *A61K 31/192* (2013.01)

(58) Field of Classification Search
CPC ........................... A61K 31/192; A61K 31/575
See application file for complete search history.

(56) References Cited

U.S. PATENT DOCUMENTS

| | | |
|---|---|---|
| 2009/0312297 A1 | 12/2009 | Hotamisligil et al. |
| 2011/0142799 A1 | 6/2011 | Glimcher et al. |
| 2012/0157419 A1 | 6/2012 | Gilat et al. |
| 2019/0255072 A1 | 8/2019 | Cohen et al. |
| 2020/0230156 A1 | 7/2020 | Cohen et al. |

FOREIGN PATENT DOCUMENTS

| | | |
|---|---|---|
| CN | 101048164 | 10/2007 |
| EP | 2422787 | 8/2010 |
| EP | 2599477 | 6/2013 |
| EP | 3016654 | 9/2018 |
| JP | 2005532372 | 10/2005 |
| JP | 2008-518935 | 6/2008 |
| JP | 2011518119 | 6/2011 |
| WO | WO 2004/096123 | 11/2004 |
| WO | WO 7006/050165 | 5/2006 |
| WO | WO 2006/086452 | 8/2006 |
| WO | WO 2009/140265 | 11/2009 |
| WO | WO 2015/001379 | 1/2015 |

OTHER PUBLICATIONS

"Alzheimer's Disease and Type 2 Diabetes: What is the Link?" Alzheimer's Association, 2011, 3 pages.
"Experimental Alzheimer Drugs Targeting Beta Amyloid and the Amyloid Hypothesis," Alzheimer's Associate, 2007, 3 pages.
"Know the 10 Signs, Early Detection Matters," Alzheimer's Association, 2009, 2 pages.
Afanas'ev, "Signaling and Damaging Functions of Free Radicals in Aging—Free Radical Theory, Hormesis. and TOR," Aging and Dis., Oct. 2010, 1(2):75-88.
Amaral et al.,. "Bile acids: regulation of apoptosis by ursodeoxycholic Acid," J Lipid Res., 2009. 50:1721-1734.
Axcan Pharma US Inc.: Treatment of Patients With All Stages of Primary Biliary Cirrhosis; URSO (ursodiol) Tablets, 250 mg: Medical Officer's Review: NDA 20-675; Mar. 26, 1996.
Basseri et al., "The chemical chaperone 4-phenylbutyrate inhibits adipogenesis by modulating the unfolded protein response," J Lipid Res., 2009, 50:2486-2501.
Biosciences Inc., "Phenylbu Tate Na Inducer, Catalog# SIH-255." StressMarq, 2011, 2 pages.
Birks, "Donepezil for dementia due to Alzheimer's disease (Review)." 2009, 75 pages.
Carducci et al., "Phenylbutyrate Induces Apoptosis in Human Prostate Cancer and Is More Potent Than Phenylacetate," Clin Canc Res., Feb. 1996, 2:379-387.
Castro et al., "The Bile Acid Tauroursodeoxycholic Acid Modulates Phosphorylation and Translocation of Bad via Phosphatidylinositol 3-Kinase in Glutamate-Induced Apoptosis of Rat Cortical Neurons." JPET, 2004, 311:845-852.
Chinese Application No. 201480017771X, First Office Action, dated Dec. 14, 2016, 13 pages (with translation).
Chiu et al., "Hepatitis C Virus Infection increases the Risk of Alzheimer's Diseases: A Population-Based Cohort Study in Taiwan." Poster, 2013, 1 page.
ClinicalTrials.gov: "Efficacy and Tolerability of Tauroursodeoxycholic Acid in Amyotrophic Lateral Sclerosis (TUDCA-ALS)", ClinicalTrials. gov, Mar. 23, 2012.
Cudkowicz et al., "Phase 2 study of sodium phenylbutyrate in ALS," Amyotrophic Lateral Sclerosis, 10(2):99-106, Apr. 2009.

(Continued)

*Primary Examiner* — Zohreh A Fay
(74) *Attorney, Agent, or Firm* — Fish & Richardson P.C.

(57) ABSTRACT

This invention relates to methods and compositions for use improving cell viability, particularly neural cell viability, and more particularly to methods and compositions for use improving cell viability by reducing reactive oxygen metabolite-mediated oxidative damage in a cell, regulating redox homeostasis in a cell, or reducing mitochondrial dysfunction in a cell. The invention further relates to the administration of the bile acid tauroursodeoxycholic acid (TUDCA) in combination with phenylbutyric Acid (PBA) to improve cell viability, and treat at least one symptom associated with, prevent the time of onset of, or slow the development of a disease related to oxidative stress.

22 Claims, 3 Drawing Sheets

(56) References Cited

OTHER PUBLICATIONS

Duan W-M et al.: "Tauroursodeoxycholic acid improves the survival and function of nigral transplants in a rat model of Parkinson's disease", Cell Transplantation, Jan. 1, 2002, 11(3):195-205.
Eckert et al., "Mitochondrial dysfunction—the beginning of the end in Alzheimer's disease? Separate and synergistic modes of tau and amyloid-β toxicity," Alzheimer's Res Therapy, 2011, 3:15, 11 pages.
Elia AE et al.: "Tauroursodeoxycholic acid in the treatment of patients with amyotrophic lateral sclerosis", *Amyotrophic Lateral Sclerosis*, Prof. Martin Maurer (Ed.), ISBN: 978-953-307-806-9, InTech, Jan. 20, 2012.
Engin et al., "Restoring endoplasmic reticulum function by chemical chaperones: an emerging therapeutic approach for metabolic diseases", Diabetes, Obesity and Metabolism, 2010, vol. 12, No. (Suppl. 2), pp. 108-115.
European Search Report in European Application No. 14775675.3, dated Nov. 7, 2016, 12 pages.
Franck et al., "Hepatitis C Virus NS2 Protein Is Phosphorylated by the Protein Kinase CK2 and Targeted for Degradation to the Proteasome," J Virol., Mar. 2005, 79(5):2700-2708.
Friedlich and Butcher, "Peer Commentary: Involvement of Free Oxygen Radicals in β-Amyloidosis: An Hypothesis," Neurobiol of Aging, 1994, 15(4):443-445.
Geula et al., "Aging renders the brain vulnerable to amyloid β-protein neurotoxicity," Nature Med., Jul. 1998, 4(7):827-831.
Gibson and Shi, "A Mitocentric View of Alzheimer's Disease Suggests Multi-Faceted Treatments," J Alzheimer's Dis., 2010. 20(2):S591-S607 (Author Manuscript).
Goh et al., "Phenylbutyrate Attenuates the Expression of Bcl-XL, DNA-PK, Caveolin-1 and VEGF in Prostate Cancer Cells," Neoplasia, 2001, 3(4):331-338.
Hayashi and Sugiyama, "4-Phenylbutyrate Enhances the Cell Surface Expression and the Transport Capacity of Wild-Type and Mutated Bile Salt Export Pumps," Hepatol., 2007, 45:1506-1516.
Hayashi and Sugiyama, "Short-Chain Ubiquitination is Associated with the Degradation Rate of a Cell-Surface-Resident Bile Salt Export Pump (BSEP/ABCB11)," Mol Pharmacol., 2009, 75:143-150.
Ho et al., "Endoplasmic Reticulum Stress Induces Tau Pathology and Forms a Vicious Cycle: Implication in Alzheimer's Disease Pathogenesis," J Alzheimer's Dis., 2012, 28:839-854.
Hoozemans et al., "The Unfolded Protein Response is Activated in Pretangle Neurons in Alzheimer's Disease Hippocampus," Am J. Pathol., Apr. 2009: 174(4):1241-1251.
Huang and Jiang, "Accumulated Amyloid-β Peptide and Hyperphosphorylated Tau Protein: Relationship and Links in Alzheimer's Disease," J Alzheimer's Dis., 2009, 16:15-27.
Inagi, "Endoplasmic Reticulum: The Master Regulator of Stress Responses in Glomerular Diseases," Intechopen, 2011, 21 pages.
International Preliminary Report on Patentability in International Application No. PCT/US2014/018040 dated Oct. 8, 2015, 8 pages.
International Search Report and Written Opinion dated Jun. 24, 2014 for International Appln. No. PCT/US2014/018040, 10 pgs.
Japanese Patent Application No. 2016-505464, First Office Action dated Oct. 3, 2017 and translation, 6 pages.
Keene, CD et al.: "Tauroursodeoxycholic acid, a bile acid is neuroprotective in a transgenic animal model of Huntington's disease", PNAS, vol. 99, No. 16, Aug. 6, 2002, pp. 10671-10676.
Kitamoto et al., "Amyloid Plaques in Creutzfeldt-Jakob Disease Stain with Prion Protein Antibodies," Ann Neurol., 1986, 20:204-208.
Lindholm et al., "ER stress and neurodenenerative diseases," Cell Death Differentiation, 2006, 13:385-392.
Liu et al., "The peroxisome proliferator phenylbutyric acid (PBA) protects astrocytes from tsl MoMuLV-induced oxidative cell death," Journal of Neurovirology, Jan. 2002, 8(4): 318-325.
Liu et al., "The peroxisome proliferator phenylbutyric acid (PBA) protects astrocytes from tsl MoMuLV-induced oxidative cell death", Journal of NeuroVirology, 8:318-325, 2002.
Marlatt et al., "Alzheimer's Disease: Cerebrovascular Dysfunction, Oxidative Stress, an Advanced Clinical Therapies," J Alzheimers Dis., 2009, 15(2):199-2010.
Marzioni et al., "Ca2+-Dependent Cytoprotective Effects of Ursodeoxycholic and Tauroursodeoxycholic Acid on the Biliary Epithelium in a Rat Model of Cholestasis and Loss of Bile Ducts," Am J Pathol., Feb. 2006, 168(2):398-409.
Material Safety Data Sheet. "Sodium Phenylbutyrate: sc-200652," May 2010, 3 pages.
Maurer M: "Amyotrophic Lateral Sclerosis: An Introduction to Treatment and Trials", Amyotrophic Lateral Sclerosis, Prof. Martin Maurer (Ed.). ISBN: 978-953-307-806-9, InTech, Jan. 20, 2012.
Miki et al., "Endoplasmic reticulum stress in diabetic hearts abolishes erythropoietin-induced myocardial protection by impairment of phospho-glycogen synthase kinase-3β-mediated suppression of mitochondrial permeability transition", Diabetes, 2009, vol. 58, pp. 2863-2872.
Min J-H et al.: "Oral sohibilized Ursodeoxycholic acid therapy in Amyotrophic Lateral Sclerosis: A randomized cross-over trial", The Journal of Korean Medical Science, vol. 27, No. 2, Jan. 27, 2012.
Mosbah et al., "Endoplasmic reticulum stress inhibition protects steatotic and non-steatotic livers in partial hepatectomy under ischemia-reperfusion," Cell Death Dis., 2010, 12 pages.
Muhammad et al., "Reactive Oxygen Species in Diabetes-induced Vascular Damage, Stroke, and Alzheimer's Disease," J Alzheimer's Dis., 2009, 16:775-785.
Niederwolfsgruber et al., "The Production of the Alzheimer Amyloid Precursor Protein (APP) in Extraneuronal Tissue Does Not Increase in Old Age," J Gerontol: Biol Sci., 1998, 53A(3):B186-B190.
Nunes et al., "TUDCA, a Bile Acid, Attenuates Amyloid Precursor Protein Processing and Amyloid-β Deposition in APP/PS1 Mice," Mol Neurobiol., 2012, 15 pages.
Office Action in Australian Application No. 2014242123, dated Feb. 22, 2018, 4 pages.
Office Action in Chinese Application No. 201480017771.X, dated Feb. 24, 2018, 10 pages (.with English translation).
Office Action in Chinese Application No. 201480017771.X, dated Nov. 8, 2018, 15 pages (with English translation).
Office Action in Japanese Application No. 2016-505464, dated Feb. 27, 2018, 5 pages (with English translation).
Office Action in Japanese Application No. 2016-505464, dated Oct. 30, 2018 6 pages (with English translation).
Parry GJ et al.: "Safety, tolerability, and cerebrospinal fluid penetration of Ursodeoxycholic Acid in patients with Amyotrophic Lateral Sclerosis", Clinical Neuropharmacology, Jan./Feb. 2010, 33(1):17-21.
Pogocki, "Alzheimer's β-amyloid peptide as a source of neurotoxic free radicals: the role of structural effects," Acta Neurobiol Exp., 2003, 63:131-145.
Qi et al., "Sodium 4-Phenylbutyrate Protects against Cerebral Ischemic Injury," Mol Pharmacol., 2004, 66:899-908.
Reagan-Shaw et al., "Dose translation from animal to human studies revisited," FASEB J., 2007, 22:659-661.
Reisberg et al., "Memantine in Moderate-to-Severe Alzheimer's Disease," N Engl J Med., 2003. 348:1333-41.
Rodrigues et al. "Amyloid β-Peptide Disrupts Mitochondrial Membrane Lipid and Protein Structure: Protective Role of Tauroursodeoxycholate," Biochem Biophys Res Comm., 2001, 281:468-474.
Roy and Kolattukudy, "Monocyte chemotactic protein-induced protein (MCPIP) promotes inflammatory angiogenesis via sequential induction of oxidative stress, endoplasmic reticulum stress and autophagy," Cellular Signalling, 2012, 24:2123-2131.
Rubio-Perez and Morillas-Ruiz, "A Review: Inflammatory Process in Alzheimer's Disease, Role of Cytokines," Scientific World J., 2012, 15 pages.
Sharma et al.., "Bile acid toxicity structure-activity relationships: Correlations between cell viability and liophilieity in a panel of new and known bile acids using an oesophageal cell line (HET- 1A)," Bioorganic & Medicinal Chemistry, Sep. 2010, 18(18): 6886-6895.
Spuch et al., "New Insights in the Amyloid-Beta Interaction with Mitochondria." J Aging Res., 2012, 9 pages.

(56) References Cited

OTHER PUBLICATIONS

Steele and Glazier, "Is donepezil effective for treating Alzheimer's disease," CA Family Physician, Apr. 1999, 45:917-919.
Suh and Checler, "Amyloid Precursor Protein, Presenilins, and α-Synuclein: Molecular Pathogenesis and Pharmacological Applications in Alzheimer's Disease," Pharmacol Rev., 2002, 54:469-525.
Sung and Waxman, "Combination of Cytotoxic-Differentiation Therapy with 5-Fluorouracil and Phenylbutyrate in Patients with Advanced Colorectal Cancer," Anticancer Res., 2007, 27:995-1002.
Sung JJ et al.: "Tauroursodeoxycholic acid (TUDCA), a bile acid, inhibits GSNO-induced apoptosis by modulating reactive oxygen species (ROS) production in motor neuronal cells expressing mutant Cu/Zn superoxide dismutase (SOD1)", Theme 4 In vitro Experimental Models, Jul. 10, 2009, 6:supl, P81, pp. 109-110.
Szweda et al., "Aging, lipofuscin formation, and free radical-mediated inhibition of cellular proteolytic systems," Ageing Res Rev., 2003, 2:383-405.
Taub, K: "TUDCA: Tauroursodeoxycholic Acid", Stanford.edu, Nov. 1, 2004, 3 pages.
Tuppo et al., "Free radical oxidative damage and Alzheimer's disease," JAOA, 2001. 101(12):S11-S15.
Vrotsos et al., "MCP-1 involvement in glial differentiation of neuroprogenitor cells through APP signaling," Brain Res Bulletin, 2009, 79:97-103.
Watson et al., "Solution Structure of Methionine-Oxidized Amyloid β-Peptide (1-40). Does Oxidation Affect Conformational Switching?" Biochem., 1998, 37:12700-12706.
Wiley et al., "Phenylbutyric Acid Rescues Endoplasmic Reticulum Stress-Induced Suppression of APP Proteolysis and Prevents Apoptosis in Neuronal Cells," PLoS One, Feb. 2010. 5(2):e9135, 17 pages.
Younce and Kolattukudy, "MCP-1 Induced Protein Promotes Adipogenesis via Oxidative Stress, Endoplasmic Reticulum Stress and Autophagy." Cell Physiol Biochem., 2012, 30:307-320.
Zhai et al., "Free radical-operated proteotoxic stress in macrophages primed with lipopolysaccharide," Free Radical Biol Med., 2012, 53:172-181.
Zhang et al., "Selective, potent blockade of the IRE1 and ATF6 pathways by 4-phenylbuyric acid analogues," British Journal of Pharmacology, Oct. 2013, 170(4): 822-834.
ALSUntangled Group, "ALSUntangled No. 25: Ursodiol," Amyotroph Lateral Scler Frontotemporal Degener., 2014, 15(5-6):475-478.
[No Author Listed] "Safety and Efficacy of TRO19622 as add-on Therapy to Riluzole Versus Placebo in Treatment of Patients Suffering From ALS (MITOTARGET)," U.S. Library of Medicine, Mar. 24, 2009, NCT00868166.
Al-Chalabi et al., "Protocol for a double-blind randomised placebo-controlled trial of lithium carbonate in patients with amyotrophic Lateral Sclerosis (LiCALS)," BMC Neurology, 2011, 11:111.
Aldini et al., "Relationship between structure and intestinal absorption of bile acids with a steroid or side-chain modification," Steroids, 1996, 61:590-597.
Andersen et al., "EFNS guidelines on the Clinical Management of Amyotrophic Lateral Sclerosis (MALS)—revised report of an EFNS task force," European Journal of Neurology, 2012, 19:360-375.
AU Office Action in Australian Appln. No. 2019200658, dated Mar. 13, 2020, 8 pages.
Berger et al., "Structure-function analysis of the tertiary bile acid TUDCA for the resolution of endoplasmic reticulum stress in intestinal epithelial cells," Biochemical and Biophysical Research Communications, 2011, 409:610-615.
Berry et al., "Design and Initial Results of a Multi-Phase Randomized Trial of Ceftriaxone in Amyotrophic Lateral Sclerosis," PLoS One, 2013, 8(4):e61177.
CA Office Action in Canadian Appln. No. 2,908,683, dated Mar. 12, 2020, 5 pages.
Dupuis et al., "A Randomized, Double Blind, Placebo-Controlled Trial of Pioglitazone in Combination with Riluzole in Amyotrophic Lateral Sclerosis," PLoS One, 7(6):e37885.
Gordon et al., "Progression in ALS is not linear but is curvilinear," J Neurol, 2010, 257:1713-1717.
KR Office Action in Korean Appln. No. 10-2015-7030684, dated Apr. 7, 2020, 8 pages (with English translation).
Leigh et al., "Amyotrophic lateral sclerosis: a consensus viewpoint on designing and implementing a clinical trial," ALS and other motor neuron disorders, 2004, 5:84-98.
Lingor et al., "ROCK-ALS: Protocol for a Randomized, Placebo-controlled, Double-Blind Phase IIa Trial of Safety, Tolerability and Efficacy of the Rho Kinase (ROCK) Inhibitor Fasudil in Amyotrophic Lateral Sclerosis," Frontiers in Neurology, 2019, 10(293):1-11.
JP Office Action in Japanese Appln. No. 2019-040563, dated Jan. 21, 2020, 10 pages (with English translation).

III

COMPOSITIONS FOR IMPROVING CELL VIABILITY AND METHODS OF USE THEREOF

CLAIM OF PRIORITY

This application is a continuation of U.S. patent application Ser. No. 16/280,861, filed Feb. 20, 2019, which is a continuation of U.S. patent application Ser. No. 15/837,866, filed Dec. 11, 2017, which is a continuation of U.S. patent application Ser. No. 14/140,083, filed on Dec. 24, 2013, which claims the benefit of U.S. Provisional Patent Application Ser. No. 61/804,690, filed on Mar. 24, 2013, the entire contents of which are hereby incorporated by reference.

TECHNICAL FIELD

This invention relates to methods and compositions for use in improving cell viability, particularly neuronal viability, and more particularly to methods and compositions for use in improving cell viability through the reduction of reactive oxygen metabolite-mediated oxidative damage in a cell, regulating redox homeostasis in a cell, or reducing mitochondrial dysfunction in a cell. This invention relates to the field of pharmaceutical treatments, and more particularly to the treatment of Alzheimer's disease and other Amyloidosis related pathology.

BACKGROUND

Neurodegenerative diseases of the central nervous system (CNS) cause progressive loss of neuronal structure and function and are devastating diseases for affected patients and their families. Among these neurodegenerative diseases are, for example, Multiple Sclerosis (MS), Parkinson's disease, Alzheimer's disease, Huntington's disease, amyotrophic lateral sclerosis (ALS) and stroke. Due to the complexity of the CNS, many of these diseases are only poorly understood to date.

Alzheimer's disease is the most prevalent neurodegenerative disease and one of the largest medical problems in the United States. In 2012, an estimated 5.4 million Americans were suffering from the disease and it was the sixth leading cause of death. As increasing age is the largest risk factor for Alzheimer's, the number of afflicted is expected to rise to 7.1 million by 2025 as the population of the United States ages. Other risk factors include certain genetic mutations, diabetes, and inflammation.

Alzheimer's disease is characterized by the aggregation of amyloid beta into plaques and the formation of neurofibrillary tangles mediated by various forms of phosphorylated tau protein. Some major symptoms of the disease include memory loss, challenges in completing and planning routine tasks, confusion with time or place, problems with words or speaking, and personality changes.

Alzheimer's is the most common member of a broad class of dementias, many of which are thought to be mediated by amyloid plaques, amyloid oligomer formation, and/or phosphorylated tau protein. These diseases include, but are not limited to, Pick's Disease, Multi-Infarct Dementia, Creutzfeldt-Jakob's Disease, Dementia with Lewy bodies, Mixed dementia, and Frontotemporal dementia.

Currently approved drugs used in the treatment of Alzheimer's disease either block NMDA-type glutamate receptors or are acetyl cholinesterase inhibitors; the latter only modestly effective for about 6-12 months in only fifty percent of patients and only under certain cognitive tests. Both classes of drugs are based on a model of increasing neural excitement globally to the generally depressed brain, making them prone to cause many side effects and doing nothing to alter disease pathology. While several drug classes are known or have been suggested for treating neurodegenerative diseases, effective therapies are scarce or non-existent. Thus, there is need for improved therapies for treating neurodegenerative diseases.

SUMMARY

At least in part, the present invention is based on the discovery that compositions comprising a bile acid (e.g., tauroursodeoxycholic acid (TUDCA)) in combination with a phenylbutyric acid (PBA) (e.g., 4-phenylbutyric acid (4-PBA)) significantly reduce reactive oxygen metabolite-mediated oxidative damage in a cell, resulting in improved cell viability (e.g., neuronal viability). As discussed in the following examples, the compounds TUDCA and 4-PBA were evaluated individually and in combination as a protectant against hydrogen peroxide-induced cell apoptosis. Hydrogen peroxide-induced cell apoptosis is thought to be caused through the altering of redox homeostasis, the overproduction of reactive oxygen species, and mitochondrial dysfunction. The examples demonstrate that TUDCA and 4-PBA, when measuring cell viability and/or cell death, have a greater than additive effect in protecting the cells against hydrogen peroxide exposure. This surprising discovery suggests that these drugs synergistically augment each other's efficacy in reducing the aforementioned pathologies.

This invention provides methods and compositions for use in improving cell viability, particularly neuronal viability, and more particularly to methods and compositions for use improving cell viability by reducing reactive oxygen metabolite-mediated oxidative damage in a cell, regulating redox homeostasis in a cell, or reducing mitochondrial dysfunction in a cell. The invention further relates to the administration of a bile acid (e.g., tauroursodeoxycholic acid (TUDCA)) in combination with a phenylbutyric acid (e.g., 4-PBA) to improve cell viability and to treat at least one symptom associated with, prevent the time of onset of, or slow the development of a disease related to oxidative stress.

The invention further provides a novel approach for reducing neuronal oxidative stress and for treating at least one symptom associated with, prevent the time of onset of, or slow the development of a disease related to oxidative stress, including but not limited to neurodegenerative diseases (e.g. Alzheimer's Disease (AD), Huntington's disease (HD), Parkinson's disease (PD), Amyotrohic Lateral Sclerosis, Pick's Disease, Multi-Infarct Dementia, Creutzfeldt-Jakob's Disease, Dementia with Lewy bodies, Frontotemporal dementia) comprising administration of a composition comprising a combination of a bile acid (e.g., tauroursodeoxycholic acid (TUDCA)) and a phenylbutyric acid (e.g., 4-PBA) or analogs, derivatives, pharmacological equivalents, or salts thereof in a pharmaceutical composition or formulation.

In one aspect, the disclosure provides a method for reducing reactive oxygen metabolite-mediated oxidative damage in a cell, the method comprising contacting the cell with a bile acid, or a pharmaceutically acceptable salt, analog, derivative, or prodrug thereof and a phenylbutyric acid (PBA), or a pharmaceutically acceptable salt, analog, derivative, or prodrug thereof. In one embodiment, the reactive oxygen metabolite-mediated oxidative damage is hydrogen peroxide ($H_2O_2$) mediated damage.

In another aspect, the disclosure provides a method of regulating redox homeostasis in a cell, the method comprising contacting the cell with a bile acid, or a pharmaceutically acceptable salt, analog, derivative, or prodrug thereof; and a phenylbutyric acid (PBA), or a pharmaceutically acceptable salt, analog, derivative, or prodrug thereof.

In yet another aspect, the disclosure provides a method of reducing mitochondrial dysfunction in a cell, the method comprising contacting the cell with a bile acid, or a pharmaceutically acceptable salt, analog, derivative, or prodrug thereof; and a phenylbutyric acid (PBA), or a pharmaceutically acceptable salt, analog, derivative, or prodrug thereof.

In one or more embodiments, the bile acid is selected from the group consisting of tauroursodeoxycholic acid (TUDCA), ursodeoxycholic acid (UDCA), chenodeoxycholic acid, cholic acid, hyodeoxycholic acid, deoxycholic acid, 7-oxolithocholic acid, lithocholic acid, iododeoxycholic acid, iocholic acid, taurochenodeoxycholic acid, taurodeoxycholic acid, glycoursodeoxycholic acid, taurocholic acid, glycocholic acid, or an analog, derivative, or derivative thereof. In some embodiments, the bile acid is selected from the group consisting of tauroursodeoxycholic acid (TUDCA), ursodeoxycholic acid (UDCA).

In some embodiments, the cell is contacted with a bile acid at a concentration of about 80 µM to about 120 µM.

In one or more embodiments, the PBA is 4-phenylbutyric acid, glycerly(Tri-4-PBA), phenyl acetic acid, 2-POAA-OMe, 2-POAA-NO2, 2-NOAA or a pharmaceutically acceptable salt, analog, derivative, or prodrug thereof.

In some embodiments, the cell is contacted a with phenylbutyric acid at a concentration of about 0.8 mM to about 1.2 mM. In some aspects, the cell is a mammalian cell. In an embodiment, the cell is a human cell. In another embodiment, the cell is a neuron.

In certain aspects, the disclosure provides a method of treating a neurodegenerative disease associated with reactive oxygen metabolite-mediated oxidative damage in a subject, the method comprising identifying a subject experiencing a neurodegenerative disease associated with reactive oxygen metabolite-mediated oxidative damage; administering to said subject a bile acid, or a pharmaceutically acceptable salt, analog, derivative, or prodrug thereof; and a phenylbutyric acid (PBA), or a pharmaceutically acceptable salt, analog, derivative, or prodrug thereof, wherein the amount of PBA administered in combination with a bile acid is reduced by 10% to 55% compared to administration of PBA alone.

In yet another aspect, the disclosure provides a method of treating a neurodegenerative disease in a subject in need thereof, the method comprising identifying a subject with at least one copy of the APOEε4 allele, administering to said subject a composition comprising a bile acid, or a pharmaceutically acceptable salt, analog, derivative, or prodrug thereof; and a phenylbutyric acid (PBA), or a pharmaceutically acceptable salt, analog, derivative, or prodrug thereof to thereby treat the neurodegenerative disease.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Diabetes, inflammation, increasing age, specific genetic variants, and many other conditions are risk factors for Alzheimer's disease. A common thread between these conditions is that they are all associated with increased free radical production, an imbalance in redox homeostasis, and/or increased free-radical mediated damage to cells and tissue. Superoxide and other free radicals have been implicated in increasing the amount of pathogenic amyloid proteins and increasing aggregation into amyloid plaques, oligomers, and other species. Without being bound by theory, this aggregation has been attributed by some to a process involving oxidation of an amino acid of the amyloid chain, especially at the Methionine 35 residue.

Incorporation of amyloid protein groups into the mitochondria has been implicated in the release of cytochrome c, oxygen radicals, and other free radicals. These radicals have been shown to increase the endoplasmic reticulum stress response and also increase the aggregation of amyloid protein.

Recent reports suggest that reactive oxygen metabolites may be involved in the pathology of Alzheimer's disease. Oxygen radicals, as well as lipid and nitrogenous radicals, are precursors in BAX, Cytochrome C, and JNK mediated pathways of apoptosis. Evidence also suggests that the alteration in redox state resultant from these species causes an increase in proteolytic activity critical in the pathology of many diseases caused at least in part by abnormal protein processing. Alteration of the cell redox state also causes a reduction in major antioxidant species such as glutathione (GSH) and vitamin E.

Reactive Oxygen Metabolite-Mediated Damage

Recent studies have also begun to implicate reactive oxygen metabolite-mediated damage as one of the major factors in neurodegenerative disease. Hydrogen peroxide, for example, has been shown to affect the mitochondria, the proteolytic state of the cell, the production of amyloid beta, redox homeostasis, and many apoptotic pathways within the cell. Hydrogen peroxide has also been shown to react with metal ions such as iron and copper to form more reactive oxygen species through Fenton chemistry. The decrease in antioxidants such as vitamin E and Glutathione in multiple neurodegenerative pathologies suggests an increase in oxidative damage in these diseases.

PINK1 and Parkin (Parkinson protein 2, E3 ubiquitin protein ligase) are thought to regulate quality control in mitochondria and mutations of these genes can be causative for Parkinson's Disease. Studies have shown that transcription of Parkin increases following the introduction of hydrogen peroxide to a cell. MPTP ((1-methyl-4-phenyl-1,2,3,6-tetra/hydropyridine) which induces Parkinson's like symptoms also results directly in the production of hydrogen peroxide. Some studies have demonstrated up to a 90% increase in hydrogen peroxide levels in this disease.

In Alzheimer's disease, amyloid beta has been shown to directly produce hydrogen peroxide when contacted with metal ions such as iron and copper, which are found in higher concentrations in the brains of patients suffering from the disease. Hydrogen peroxide may also increase the processing of amyloid beta into a pathogenic form. Hydrogen peroxide and reactive oxygen-metabolite mediated pathways are also thought to be a major route of cell death in this disease.

Huntington's disease also shows proteolytic products likely to be caused by hydrogen peroxide, as well as widespread mitochondrial dysfunction. The increase in 3-hydroxykyneurine has been implicated as a major pathological step in Huntington's disease and is known to directly induce hydrogen peroxide and hydroxyl radical production.

Hydrogen peroxide has also been shown to be a potential mediator in the pathology of ALS. Scavengers of hydrogen peroxide have been considered as therapeutics in this field.

Regulation of Redox Homeostasis

Redox homeostasis refers to the attempt of a cell to manage reductive and oxidative species in the cell to maintain a constant redox state. Disruptions in redox homeostasis may change free energy requirements and allow processes to take place in cells that would not occur under non-pathologic conditions. Some processes that may be caused by failure of regulation of redox homeostasis include the aggregation of amyloid beta into plaques characteristic of Alzheimer's disease, the Lewy Bodies of Parkinson's disease and Dementia with Lewy Bodies, the senile plaques of Huntington's disease, the plaques including amyloid plaques that have been found in ALS, and the disorders of tauopathies. Under typical physiological conditions these proteins will not aggregate, but increased concentrations as well as atypical redox states are thought to alter the free energy of aggregation resulting in the observed plaques in these pathologies. Altered redox state can also produce free radicals which interact with mitochondrial pathways to induce apoptosis. A need therefore exists to develop an agent that can aid in regulation of the redox state of a cell. Since Hydrogen Peroxide induces altered redox state of a cell it can be used to cause redox-mediated damage to a cell.

Mitochondrial Dysfunction

Mitochondrial dysfunction is widespread in neurodegenerative disease. In Alzheimer's disease, the mitochondrial membrane potential of cells is markedly reduced, glucose metabolism by the mitochondria is impaired, and the permeability of the mitochondria is increased. Mitochondria have been observed to mediate multiple apoptotic pathways resulting in neuronal death in Alzheimer's disease.

PINK1 and Parkin are both mitochondrial quality control proteins. Mutations or lack of these proteins is strongly linked to Parkinson's disease. MPTP, a molecule used to induce permanent symptoms of Parkinson's, acts through the disruption of complex I of the mitochondria, causing mitochondrial dysfunction, alteration of the redox state of the cell, and apoptosis.

It has been directly shown in cell culture that the mutant Huntingtin gene and its resultant protein, thought to be the primary mediator of Huntington's disease, results in a loss of membrane potential and decreased expression of critical oxidative phosphorylation genes in the mitochondria. Huntington's disease pathology has also been linked to a decrease in the number of mitochondria present in the central nervous system.

Mitochondrial dyslocalization, energy metabolism impairment, and apoptotic pathways are thought to mediate Amyotrophic lateral sclerosis. Mitochondria from affected tissues have also been shown to overproduce reactive oxygen metabolites and leak them to the cytosol.

In many neurodegenerative diseases, mitochondria overproduce free radicals, cause a reduction in energy metabolism, have increased permeability, have decreased membrane potential, have decreased antioxidants, leak metal ions into the cell, alter the redox state of the cell, and lead the cell down pro-apoptotic pathways. A need therefore exists for agents that can alter and reduce mitochondrial dysfunction mechanisms. APOEε4 Allele The genetics of Alzheimer's disease is complex. Mutations in at least four genetic loci are associated with inherited susceptibility to AD (i.e., familial AD). Three genes have been associated with early onset AD: APP [β-amyloid precursor protein on chromosome 21], PS1 (presenilin 1) and PS2 (presenilin 2). The ε4 allele of the apolipoprotein E (APOE) gene on chromosome 19 has been associated with late onset AD. The association of APOEε4 with AD appears to be strongest in individuals with an onset prior to 70 years of age and weakens with advanced age. Patients who present with at least one copy of the APOE ε4 allele have been shown to have particularly elevated levels of peroxide metabolites as well as mitochondrial damage. Treatment to this patient population may be particularly effective.

In certain aspects, the disclosure contemplates a method of treating a neurodegenerative disease in a subject in need thereof, the method comprising identifying a subject with at least copy of the APOEε4 allele, administering to said subject a composition comprising a bile acid, or a pharmaceutically acceptable salt, analog, derivative, or prodrug thereof; and a phenylbutyric acid (PBA), or a pharmaceutically acceptable salt, analog, derivative, or prodrug thereof to thereby treat the neurodegenerative disease.

In certain aspect, the invention provides methods comprising contacting a cell with a bile acid. As used herein, "bile acid" (e.g., aqueous soluble bile acid derivatives, bile acid salts, or bile acid conjugated with an amine) refers to naturally occurring surfactants having a nucleus derived from cholanic acid substituted with a 3α-hydroxyl group and optionally with other hydroxyl groups as well, typically at the $C_6$, $C_7$ or $C_{12}$ position of the sterol nucleus. Bile acid derivatives include, but are not limited to derivatives formed at the hydroxyl and carboxylic acid groups of the bile acid with other functional groups including but not limited to halogens and amino groups. Soluble bile acid may include an aqueous preparation of a free acid form of bile acid combined with one of HCl, phosphoric acid, citric acid, acetic acid, ammonia, or arginine.

Figure 3:
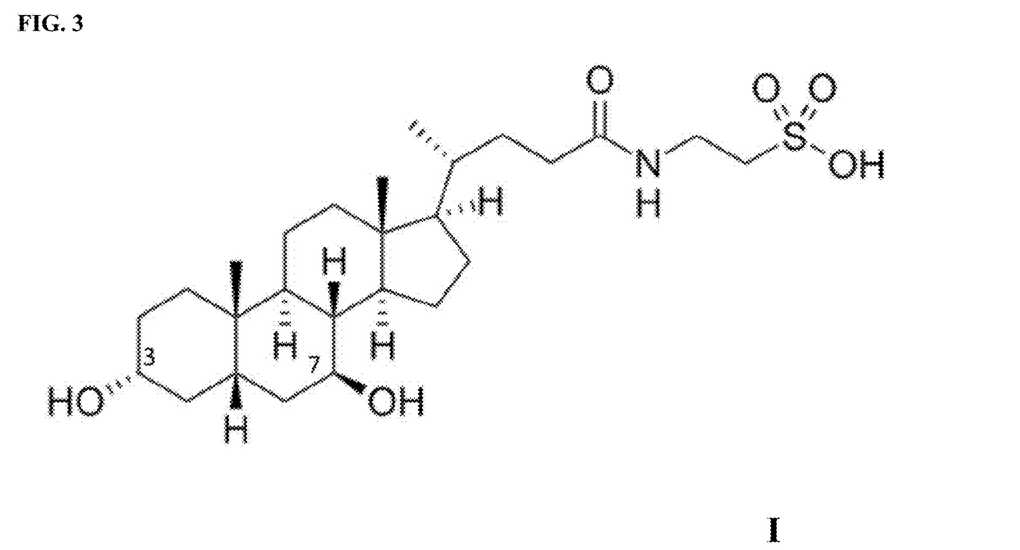
FIG. 3 demonstrates the chemical structure of TUDCA (formula I) with labeled carbons to assist in understanding where substitutions can be made.

In certain aspects, the methods of the present invention comprise contacting a cell with a bile acid, or a pharmaceutically acceptable salt, analog, derivative, or prodrug thereof. In one or more embodiments, the bile acid is tauroursodeoxycholic acid (TUDCA) as shown in formula I (FIG. 3), with labeled carbons to assist in understanding where substitutions may be made.

Figure 4:
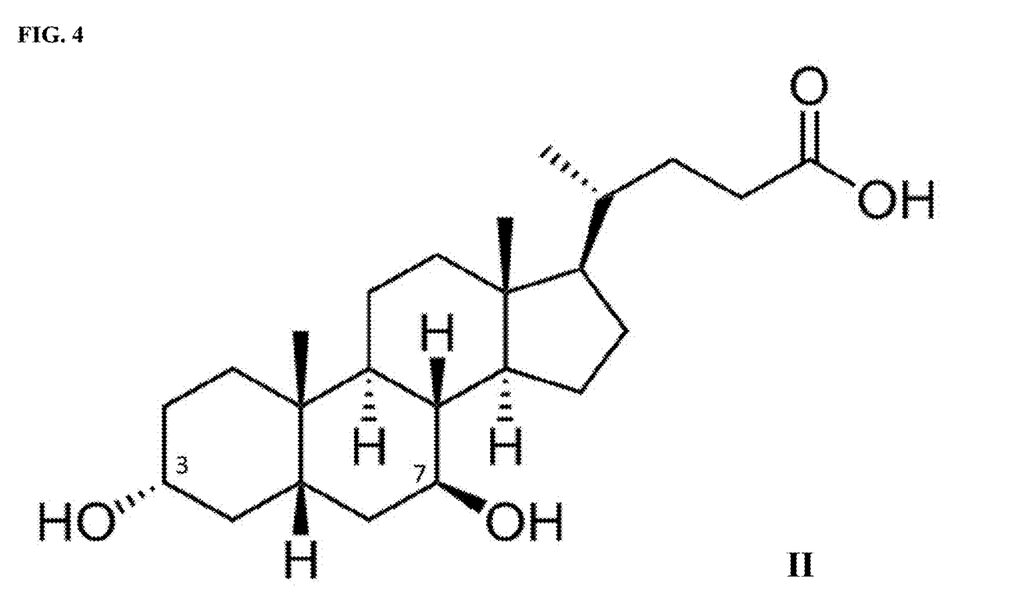
FIG. 4 demonstrates the chemical structure of UDCA (formula II) with labeled carbons to assist in understanding where substitutions can be made.
Figure 5:
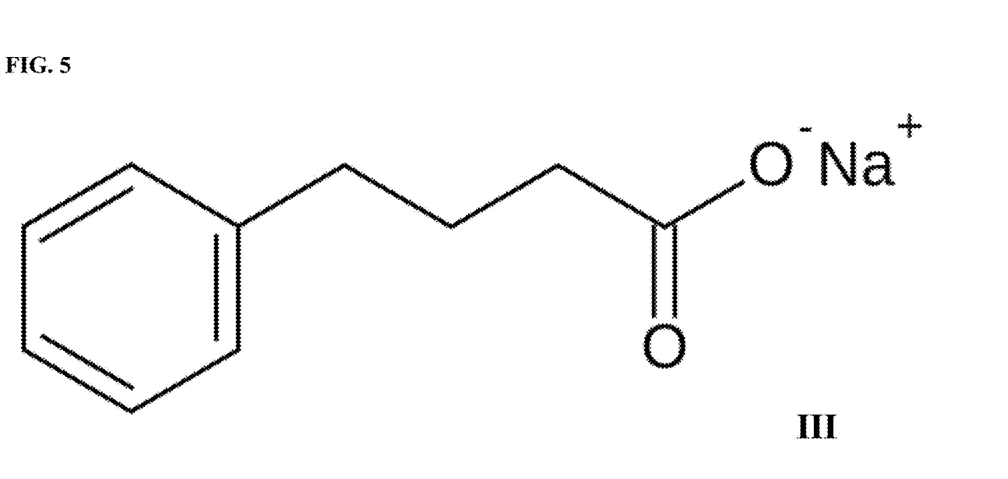
FIG. 5 demonstrates the chemical structure of PBA stabilized by sodium ion (formula III). Derivatives available for use under this invention are described in the background.

In one or more embodiments, the bile acid ursodeoxycholic acid (UDCA) as shown in formula II (FIG. 4), with labeled carbons to assist in understanding where substitutions may be made.

Physiologically related bile acid derivatives include any combination of substitutions of hydrogen at position 3 or 7, a shift in the stereochemistry of the hydroxyl group at positions 3 or 7, and pharmaceutically acceptable salts, solvates or amino acid conjugates thereof of TUDCA or UDCA.

In some embodiments, the bile acid is a TUDCA compound of formula IV:

wherein R is —H or $C_1$-$C_4$ alkyl;
$R_1$ is —$CH_2$—$SO_3R_3$ and $R_2$ is —H; or $R_1$ is —COOH and $R_2$ is —$CH_2$—$CH_2$—$CONH_2$, —$CH_2$—$CONH_2$, —$CH_2$—$CH_2$—$SCH_3$ or —$CH_2$—S—$CH_2$—COOH; and
$R_3$ is —H or the residue of a basic amino acid, or a pharmaceutically acceptable analog, derivative, prodrug thereof, or a mixture thereof, This invention also contemplates the use of bile acids in addition to TUDCA and UDCA, including, for example, chenodeoxycholic acid (also referred to as "chenodiol" or "chenic acid"), cholic acid, hyodeoxycholic acid, deoxycholic acid, 7-oxolithocholic acid, lithocholic acid, iodedeoxycholic acid, iocholic acid, taurochenodeoxycholic acid, taurodeoxycholic acid, glycoursodeoxycholic acid, taurocholic acid, glycocholic acid, cholic acid, or an analog, derivative, or derivative thereof.

In certain aspect, the invention provides methods comprising the contacting a cell with a phenylbutyric acid. Phenylbutyric acid (PBA) (FIG. 4, sodium salt) is a HDAC2 (Histone Deacetylase 2) inhibitor. Uptake of PBA and derivatives results in differential gene expression which has been shown to have a variety of effects. PBA has also been shown to act as a chemical chaperone with a variety of effects. One effect is the decrease in production of pathogenic amyloid protein. Another effect is increased neuroplasticity. PBA has also been shown to improve biliary excretion. PBA is however known to be cytotoxic to multiple different cell types.

Physiologically related phenylbutyric acid (PBA) species include any substitutions for Hydrogens with Deuterium. Any salts, solvates, conjugates and pharmacologically related compounds will also be considering physiologically related. Also all phenylbutyric acid derivatives described in Prior Art will be considered physiologically related. Other HDAC2 inhibitors will also be considered as substitutes for phenylbutyrate. Phenylacetic acid, the active metabolite of PBA may also be considered as a substitute.

In one or more embodiments the PBA compound is 4-Phenylbutyric acid (4-PBA). 4-PBA is a low molecular weight aromatic carboxylic acid. 4-PBA is defined herein as encompassing not only 4-Phenybutyric acid as a free acid but also its derivatives and physiologically acceptable salts thereof. Especially, "4-Phenylbutyric acid" or "4-PBA" is also defined as its free acid, but also as being in the form of a pharmaceutically acceptable salt, co-crystal, polymorph, hydrate, solvate or pro-drug of 4-phenylbutyric acid. Most preferably, "4-Phenylbutyric acid" or "4-PBA" is either the free acid or a pharmaceutically acceptable salt of 4-PBA, such as its sodium salt. Analogs of 4-PBA included, for example, Glycerly(Tri-4-PBA), Phenyl Acetic Acid, 2-POAA-OMe, 2-POAA-NO2, 2-NOAA. Physiologically acceptable salts of 4-phenylbutyrate, include, for example sodium, potassium, magnesium or calcium salts.

Pharmaceutical Compositions and Methods of Administration

In certain aspects, the methods described herein include the manufacture and use of pharmaceutical compositions and medicaments that include compounds identified by a method described herein as active ingredients. Also included are the pharmaceutical compositions themselves.

In some instances, the compositions disclosed herein can include other compounds, drugs, and/or agents used for the treatment of neurodegenerative disease. For example, in some instances, therapeutic compositions disclosed herein can be combined with one or more (e.g., one, two, three, four, five, or less than ten) compounds.

In some instances, the compositions disclosed herein can include other compounds including COX2 inhibitors, asthma drugs, diabetes drugs, other antioxidants, acetyl cholinesterase inhibitors (e.g., donepezil, tacrine, rivastigmine, galantamine, physostigmine, neostigmine, Huperzine A, icopezil (CP-118954, 5,7-dihydro-3-[2-[1-(phenylmethyl)-4-piperidinyl]ethyl]-6H-pyrrolo-[4,5-f]-1,2-benzisoxazol-6-one maleate), ER-127528 (4-[(5,6-dimethoxy-2-fluoro-1-indanon)-2-yl]methyl-1-(3-fluorobenzyl) piperidine hydrochloride), zanapezil (TAK-147; 3-[1-(phenylmethyl)piperidin-4-yl]-1-(2,3,4,5-tetrahydro-1H-1-benzazepin-8-yl)-1-propane fumarate), Metrifonate (T-588; (−)-R-a-[[2-(dimethylamino)ethoxy]methyl]benzo[b]thiophene-5-methanol hydrochloride), FK-960 (N-(4-acetyl-1-piperazinyl)-p-fluorobenzamide-hydrate), TCH-346 (N-methyl-N-2-pyropinyldibenz[b,f] oxepine-10-methanamine), SDZ-220-581 ((S)-a-amino-5-(phosphonomethyl)-[1,1'-biphenyl]-3-propionic acid), and combinations thereof), NMDA receptor antagonists (e.g., memantine, neramexane, rimantadine, or amantadine, lipoxygenase inhibitors, leukotriene inhibitors, coconut oil, other HDAC inhibitors, statins, amphetamines, other MAO inhibitors, metal chelators, BACE1-inhibitors, antibodies to amyloid beta, gamma-secretase modulators, amyloid clearing agents, phosphorylated tau antibodies, Aβ inhibitors, Aβ plaque removal agents, inhibitors of Aβ plaque formation, inhibitors of amyloid precursor protein processing enzymes, β-amyloid converting enzyme inhibitors, β-secretase inhibitors, γ-secretase modulators, nerve growth factor agonists and neurofibrillary tangle clearing agents).

In some instances, compositions disclosed herein can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm). The pharmaceutical compositions may be formulated for oral, parenteral, or transdermal delivery. The compound of the invention may also be combined with other pharmaceutical agents. In some aspects, the invention provides kits that include the TUDCA and PBA compounds used in the invention. The kit may also include instructions for the physician and/or patient, syringes, needles, box, bottles, vials, etc. In an aspect, the invention provides methods and agents that are useful in preventing or treating neurodegenerative disease, including Multiple Sclerosis (MS), Parkinson's disease, Alzheimer's disease, Huntington's disease, amyotrophic lateral sclerosis (ALS), stroke, Pick's Disease, Multi-Infarct Dementia, Creutzfeldt-Jakob's Disease, Dementia with Lewy bodies, Mixed dementia, Frontotemporal dementia, and associated diseases. In particular, the invention provides agents or pharmaceutical compositions that can be used to treat or prevent Alzheimer's disease and other amyloidosis related pathologies, and prevent complications of these conditions.

In some instances, pharmaceutical compositions can include an effective amount of a bile acid and a phenylbutyric acid as described above. The terms "effective amount" and "effective to treat," as used herein, refer to an amount or a concentration of one or more drugs for a period of time (including acute or chronic administration and periodic or continuous administration) that is effective within the context of its administration for causing an intended effect or physiological outcome.

In some instances, pharmaceutical compositions can include of a bile acid (e.g., TUDCA), a phenylbutyric acid (e.g., 4-PBA), and any pharmaceutically acceptable carrier, adjuvant and/or vehicle. In some instances, pharmaceuticals can further include one or more additional therapeutic agents in amounts effective for achieving a modulation of disease or disease symptoms.

Pharmaceutical compositions typically include a pharmaceutically acceptable carrier. The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound. As used herein the language "pharmaceutically acceptable carrier" includes saline, solvents, dispersion media, coatings, antibacterial and antifungal agents, isotonic and absorption delaying agents, and the like, compatible with pharmaceutical administration.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intraarterial, intrasynovial, intrasternal, intrathecal, intralesional and intracranial injection or infusion techniques.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some embodiments, the present disclosure provides methods for using a composition comprising a bile acid (e.g., TUDCA) and a phenylbutyric acid (e.g., 4-PBA), including pharmaceutical compositions, (indicated below as 'X') disclosed herein in the following methods:

Substance X for use as a medicament in the treatment of one or more diseases or conditions disclosed herein (e.g., neurodegenerative disease, referred to in the following examples as 'Y'). Use of substance X for the manufacture of a medicament for the treatment of Y; and substance X for use in the treatment of Y.

In some instances, therapeutic compositions disclosed herein can be formulated for sale in the US, import into the US, and/or export from the US.

The pharmaceutical compositions can be included in a container, pack, or dispenser together with instructions for administration.

Dosage

In some aspects of the invention, TUDCA (Tauroursodeoxycholic Acid) and PBA (4-Phenylbutyrate), are individually administered (i.e., separate dosage forms). In some embodiments, TUDCA is administered in amount of about 10 mg/kg body weight, about 15 mg/kg body weight, about 20 mg/kg body weight, about 30 mg/kg body weight, about 40 mg/kg body weight, or about 40 mg/kg body weight. In some embodiments, PBA is administered in amount of about 10 mg/kg body weight, about 30 mg/kg body weight, about 50 mg/kg body weight, about 100 mg/kg body weight, about 200 mg/kg body weight, or about 400 mg/kg body weight. The compounds can be administered separately or together, including as a part of a regimen of treatment.

The invention further provides dosing regimens, such that the TUDCA and/or PBA dosage forms are administered, separately or together, as a single daily dosage, on a daily basis, a weekly basis or some other basis. Further, the patient may receive the specific dosage over a period of weeks, months, or years. For example, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years and the like.

Advantages of the compositions of the invention, include, (1) smaller solid PBA dosage form size; and (2) smaller doses of PBA required to obtain the same pharmacological effect. Thus, in certain aspects, this invention provides improved methods for treating neurodegenerative disease that comprise administering a PBA, in combination with a bile acid, in a reduced dosage amount compared with treatment of neurodegenerative diseases with PBA (e.g., compared with standard dosing amounts of PBA). In some embodiments, the amount of PBA administered in combination with a bile acid is reduced by about 10%, about 15%, about 20%, about 25%, about 30%, about 40%, about 45%, about 50%, or about 55% compared to the dosage amount used what PBA is administered alone.

Methods of Treatment

The methods described herein include methods for the treatment of disorders associated with cellular oxidative stress (e.g., reactive oxygen metabolite-mediated oxidative damage in a cell, redox imbalance in a cell, or mitochondrial dysfunction in a cell). In some embodiments, the disorder is a neurodegenerative disease (e.g., Alzheimer's disease (AD), Huntington's disease (HD), Parkinson's disease (PD), Amyotrohic Lateral Sclerosis). Generally, the methods include administering a therapeutically effective amount of a bile acid (e.g., TUDCA) in combination with a phenylbutyric acid (e.g., 4-PBA) as described herein, to a subject (e.g., a mammalian subject, e.g., a human subject) who is in need of, or who has been determined to be in need of, such treatment.

In some instances, methods can include selection of a human subject who has or had a condition or disease. In some instances, suitable subjects include, for example, subjects who have or had a condition or disease but that resolved the disease or an aspect thereof, present reduced symptoms of disease (e.g., relative to other subjects (e.g., the majority of subjects) with the same condition or disease), and/or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease).

The methods disclosed herein can be applied to a wide range of species, e.g., humans, non-human primates (e.g., monkeys), horses, cattle, pigs, sheep, deer, elk, goats, dogs, cats, rabbits, guinea pigs, hamsters, rats, and mice.

The terms "treat", "treating", "treatment", etc., as applied to an isolated cell, include subjecting the cell to any kind of process or condition or performing any kind of manipulation or procedure on the cell. As applied to a subject, the term "treating" refer to providing medical or surgical attention, care, or management to an individual. The individual is usually ill or injured, or at increased risk of becoming ill relative to an average member of the population and in need of such attention, care, or management.

In some embodiments, the term "treating" and "treatment" refers to administering to a subject an effective amount of a composition, e.g., a composition comprising a bile acid and a phenylbutyric acid, so that the subject has a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. In some embodiments, treatment can be "prophylaxic treatment, where the subject is administered a composition as disclosed herein (e.g., a composition comprising a bile acid and a phenylbutyric acid) to a subject at risk of developing a neurodegenerative disease as disclosed herein. In some embodiments, treatment is "effective" if the progression of a disease is reduced or halted.

The term "subject," as used herein, refers to any animal. In some instances, the subject is a mammal. In some instances, the term "subject", as used herein, refers to a human (e.g., a man, a woman, or a child).

In some instances, subject selection can include obtaining a sample from a subject (e.g., a candidate subject) and testing the sample for an indication that the subject is suitable for selection. In some instances, the subject can be confirmed or identified, e.g. by a health care professional, as having had or having a condition or disease. In some instances, exhibition of a positive immune response towards a condition or disease can be made from patient records, family history, and/or detecting an indication of a positive immune response. In some instances multiple parties can be included in subject selection. For example, a first party can obtain a sample from a candidate subject and a second party can test the sample. In some instances, subjects can be selected and/or referred by a medical practitioner (e.g., a general practitioner). In some instances, subject selection can include obtaining a sample from a selected subject and storing the sample and/or using the in the methods disclosed herein. Samples can include, for example, cells or populations of cells.

In some instances, treatments methods can include a single administration, multiple administrations, and repeating administration as required for the prophylaxis or treatment of the disease or condition from which the subject is suffering. In some instances treatment methods can include assessing a level of disease in the subject prior to treatment, during treatment, and/or after treatment. In some instances, treatment can continue until a decrease in the level of disease in the subject is detected.

The terms "administer," "administering," or "administration," as used herein refers to implanting, absorbing, ingesting, injecting, or inhaling, the inventive drug, regardless of form. In some instances, one or more of the compounds disclosed herein can be administered to a subject topically (e.g., nasally) and/or orally. For example, the methods herein include administration of an effective amount of compound or compound composition to achieve the desired or stated effect. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Following administration, the subject can be evaluated to detect, assess, or determine their level of disease. In some instances, treatment can continue until a change (e.g., reduction) in the level of disease in the subject is detected.

Upon improvement of a patient's condition (e.g., a change (e.g., decrease) in the level of disease in the subject), a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

EXAMPLES

The invention is further described in the following examples, which do not limit the scope of the invention described in the claims.

Materials and Methods:

Compounds were tested in peroxide exposure neuronal cell model at Charles River Labs Discovery Research Services Finland as described herein.

Cortical mixed cultures were prepared from E18 Wistar rat embryos (Laboratory Animal Center, Kuopio, Finland). The cortices were dissected out and the tissue was cut to small pieces. The cells were separated by 15-min incubation with DNase and papain. The cells were collected by centrifugation (1500 rpm, 5 min). The tissue was triturated with a pipette and the cells were plated ($3 \times 10^5$ cells/cm$^2$) on poly-L-lysine coated 48 wells in MEM supplemented with 2 g/l glucose, 2 mM glutamine, 0.1 µg/ml gentamicin, and 10% heat-inactivated horse serum (HS-HI) and heat-activated bovine serum (FBS-HI). After three days in vitro, medium containing MEM with supplements and 5% both sera was changed to the cells. On day 6 in vitro, the unwanted cell division was inhibited by adding cytosine arabinoside (10 µM final concentration) for 24 h. The cultures were refed with MEM with supplements and 5% HS-HI before experiments.

The wells in good shape were chosen for experiment on day 10 in vitro. Test compounds were diluted in MEM with supplements and 5% HS-HI. 24 h later, 300 µM NMDA for 24 h was used as a control for total neuronal death, and $H_2O_2$ for 1 h was used to induce approximately 30-60% cell death. DFX (100 µM) was used as a potential positive control for inhibition of $H_2O_2$-induced cell death. Wells treated with medium only served as 0-control. Test compounds were pipetted to the cells 24 h before adding $H_2O_2$. After 60 min, the medium was removed and media containing the compounds was pipetted to the wells for 24 h.

After 24 h the culture media of all wells was collected and possible cell debris was removed by centrifugation (13 000 rpm, 3 min). A-100-µl aliquot was pipetted into a micro titer plate as duplicates, and equal amount of LDH reagent was pipetted to the wells. The absorbance at 340 nm was measured immediately using a 3-min kinetic measurement protocol in Multiskan Ascent ELISA reader (Thermo, Finland). The change in absorbance/min was determined, which is directly proportional to the released LDH (=cell death).

After the cell culture medium was collected for LDH measurement, 100 µl PrestoBlue solution (1:10 dilution of PrestoBlue reagent (Invitrogen, #A13261, lot 915815C) in culture medium) was added to the wells for 1 h incubation at +37° C. $CO_2$ incubator. Fluorescence at 560 nm excitation/615 nm emission was measured using Victor fluororeader (PerkinElmer).

The number of wells per compound concentration used was 6 (n=6). One (1) concentration of 100 µM TUDCA and 1 mM 4-PBA separately and together were studied. Statistical analysis were calculated on Microsoft excel. The values were analyzed two-tailed, equal variance t-tests comparing all conditions to all other conditions.

Example 1

The inventors tested TUDCA and 4-PBA in combination in a peroxide exposure neuronal cell model to explore what effects they may have in concert. A peroxide exposure neuronal cell model was chosen for its correlation with oxidative stress and pathology in various neurodegenerative diseases. In this study, the inventors evaluated efficacy based on cell viability and cell death.

Figure 1:
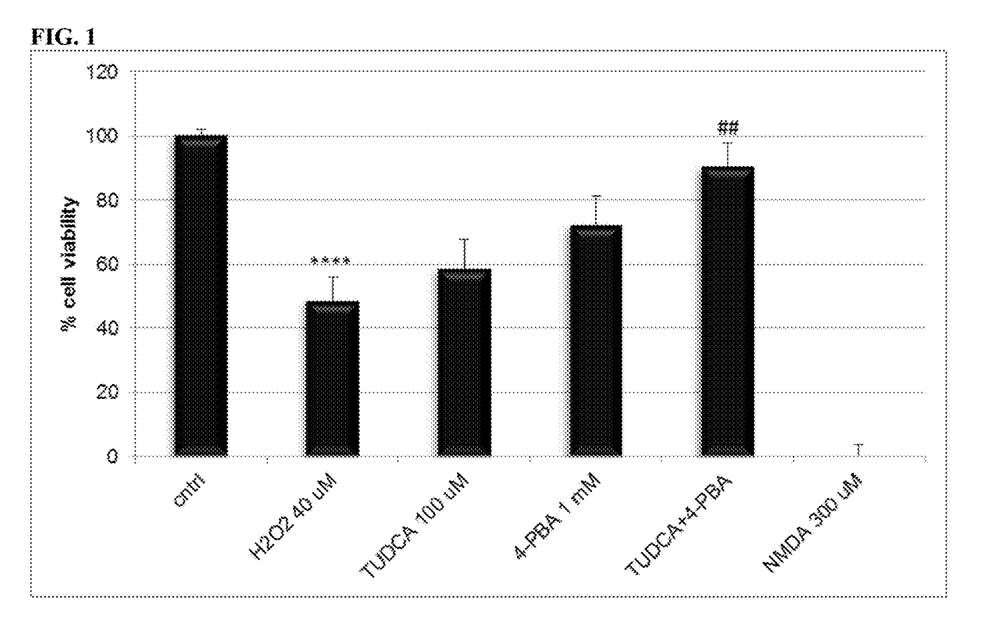
FIG. 1 is a graph demonstrating the ability of TUDCA and PBA in combination to increase cell viability evaluated by PrestoBlue after Hydrogen Peroxide exposure in rat cortical neuron culture. **** denotes significance of $p<0.0001$ against control. ## denotes significance of $p<0.01$ against peroxide exposure. # denotes significance of $p<0.05$ against peroxide exposure. The combination provides significant protection while each drug individually does not provide significant protection. NMDA exposure at 300 uM is used as a negative control. DFX (not shown) was not included in the plot as it is thought to interfere with PrestoBlue measurement and provided erratic results.

Use of TUDCA and 4-PBA, in combination, resulted in a 90.4% cell viability, a statistically significant improvement over control cell viability of 48.6% (p<0.003). (FIG. 1, Table 1) Individual treatments with TUDCA and 4-PBA resulted in cell viabilities of 59% and 72% respectively, not significantly different from control (p<0.414 and p<0.071 respectively). (FIG. 1, Table 1) The combination therefore causes a 24% increase in efficacy over the sum efficacy of the individual drug treatments. NMDA at 300 uM was used as a negative control and resulted in about 0% cell viability. DFX provided the erratic result of about 11% less cell viability than the peroxide exposure condition. This result was thought to be due to DFX interfering with the PrestoBlue measurement mode so this result was excluded. Efficacy is calculated as absolute difference in mean viability from mean viability of control.

The near return to control provided by the combination of molecules as seen in the PrestoBlue study is truly surprising and highlights the potential for this combination as a therapy for diseases related to peroxide toxicity. The combination improved viability and decreased cell death more than the sum of the benefits provided by each compound alone.

TABLE 1

Cell Viability Evaluated By PrestoBlue Following $H_2O_2$ Exposure

|  | Average (%) | Standard Error (%) |
|---|---|---|
| No Treatment | 100.00 | 2.21 |
| $H_2O_2$ 40 uM | 48.56 | 7.45 |
| TUDCA 100 uM | 58.59 | 9.10 |
| 4-PBA 1 mM | 72.20 | 9.01 |
| TUDCA + 4-PBA 100 um and 1 mM respectively | 90.39 | 7.40 |
| DFX 100 uM | 37.49 | 3.72 |
| NMDA 300 uM | 0.00 | 2.73 |

Figure 2:
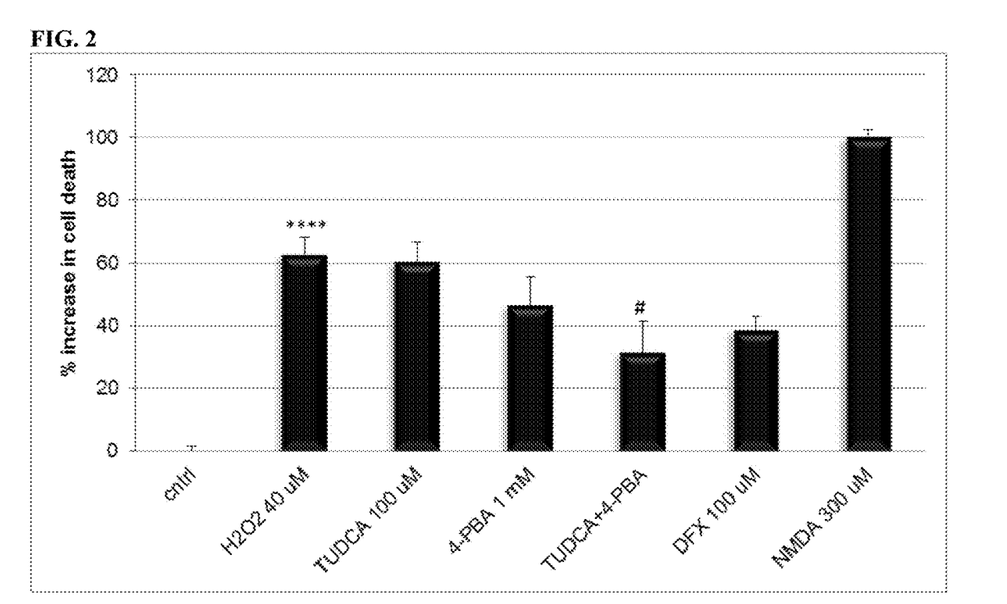
FIG. 2 is a graph demonstrating the ability of TUDCA and PBA in combination to ameliorate cell death evaluated by LDH after Hydrogen Peroxide ($H_2O_2$) exposure in rat cortical neuron culture. **** denotes significance of $p<10-4$ against control. ## denotes significance of $p<0.01$ against peroxide exposure. # denotes significance of $p<0.05$ against peroxide exposure. The combination provides significant protection while each drug individually does not provide significant protection. NMDA exposure at 300 uM is used as a negative control while DFX is a positive control in the LDH study.

Use of TUDCA and 4-PBA, in combination, resulted in a 31.5% cell death percentage, a statistically significant improvement over control cell death percentage of 62.5% (p<0.021). (FIG. 2) Individual treatments with TUDCA and 4-PBA resulted in cell death percentages of 60.4% and 46.5% respectively, not significantly different from control (p<0.808 and p<0.162 respectively). (FIG. 2) The combination therefore causes a 71% increase in efficacy over the sum efficacy of the individual drug treatments. DFX and NMDA were used as positive and negative controls respectively and resulted in 38.5% and 100% cell death respectively. Efficacy is calculated as absolute difference in mean viability from mean viability of control.

These surprising and synergistic results suggest the combination of TUDCA and 4-PBA may be a novel, efficacious, and potent treatment to reactive oxygen metabolite-mediated oxidative damage, and thereby reducing neuronal oxidative stress and to treat at least one symptom associated with, prevent the time of onset of, or slow the development of a disease associated with oxidative stress.

TABLE 2

Cell Death Evaluated By LDH Following $H_2O_2$ Exposure

|  | Average (%) | standard error (%) |
|---|---|---|
| No Treatment | 0.00 | 1.25 |
| $H_2O_2$ 40 uM | 62.48 | 13.09 |
| TUDCA 100 uM | 60.37 | 11.75 |
| 4-PBA 1 mM | 46.47 | 11.05 |
| TUDCA + 4-PBA 100 um and 1 mM respectively | 31.52 | 9.50 |
| DFX 100 uM | 38.50 | 8.58 |
| NMDA 300 uM | 100.00 | 16.90 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating at least one symptom of Amyotrophic Lateral Sclerosis (ALS) in a human subject, the method comprising administering to the subject about 10 mg/kg to about 30 mg/kg of body weight of tauroursodeoxycholic acid (TUDCA) and about 30 mg/kg to about 100 mg/kg of body weight of sodium phenylbutyrate.

2. The method of claim 1, wherein the TUDCA is administered once a day.

3. The method of claim 1, wherein the sodium phenylbutyrate is administered once a day.

4. The method of claim 1, wherein the TUDCA and the sodium phenylbutyrate are administered once a day.

5. The method of claim 1, wherein the TUDCA and sodium phenylbutyrate are administered as separate dosage forms.

6. The method of claim 1, wherein the TUDCA and sodium phenylbutyrate are administered in a single dosage form.

7. The method of claim 1, wherein the TUDCA is administered at an amount of about 0.5 to about 5 grams per day.

8. The method of claim 1, wherein the TUDCA is administered at an amount of about 1.5 to about 2.5 grams per day.

9. The method of claim 1, wherein the TUDCA is administered at an amount of 1 gram twice a day.

10. The method of claim 1, wherein the sodium phenylbutyrate is administered at an amount of about 0.5 to about 10 grams per day.

11. The method of claim 1, wherein the sodium phenylbutyrate is administered at an amount of about 4.5 to about 8.5 grams per day.

12. The method of claim 1, wherein the sodium phenylbutyrate is administered at an amount of 3 grams twice a day.

13. The method of claim 1, wherein the TUDCA and the sodium phenylbutyrate are administered to the subject for less than 6 months.

14. The method of claim 1, wherein the TUDCA and the sodium phenylbutyrate are administered to the subject for less than 3 months.

15. The method of claim 1, wherein the TUDCA and the sodium phenylbutyrate are administered to the subject for at least 6 months.

16. The method of claim 1, wherein the administering is oral administration.

17. The method of claim 1, wherein the human subject is suspected as having ALS.

18. The method of claim 1, wherein the human subject has been diagnosed as having a condition associated with ALS.

19. The method of claim 1, wherein the TUDCA is administered at an amount of 1 gram twice a day and the sodium phenylbutyrate is administered at an amount of 3 grams twice a day, wherein the TUDCA and sodium phenylbutyrate are administered in a single dosage form, and wherein the administering is oral administration.

20. The method of claim 1, wherein the TUDCA is administered twice a day.

21. The method of claim 1, wherein the sodium phenylbutyrate is administered twice a day.

22. The method of claim 1, wherein the TUDCA and the sodium phenylbutyrate are administered twice a day.

* * * * *

UNITED STATES PATENT AND TRADEMARK OFFICE
CERTIFICATE OF CORRECTION

PATENT NO. : 10,857,162 B2  
APPLICATION NO. : 16/781239  
DATED : December 8, 2020  
INVENTOR(S) : Joshua Cohen and Justin Klee Page 1 of 1

It is certified that error appears in the above-identified patent and that said Letters Patent is hereby corrected as shown below:

On the Title Page

Column 2 (item (56) Foreign Patent Documents), Line 3, delete "WO 7006/050165" and insert -- WO 2006/050165 --

Column 2 (item (56) Other Publications), Line 8, delete "Hormesis." and insert -- Hormesis, --

Column 2 (item (56) Other Publications), Line 10, delete "al.,." and insert -- al., --

Column 2 (item (56) Other Publications), Line 11, delete "2009." and insert -- 2009, --

Column 2 (item (56) Other Publications), Line 13, delete "250 mg:" and insert -- 250 mg; --

Column 2 (item (56) Other Publications), Line 14, delete "Review:" and insert -- Review; --

Column 2 (item (56) Other Publications), Line 18, delete ""Phenylbu Tate" and insert -- "Phenylbutyrate --

Column 2 (item (56) Other Publications), Line 18, delete "SIH-255."" and insert -- SIH-255," --

Column 2 (item (56) Other Publications), Line 20, delete "(Review)."" and insert -- (Review)," --

Column 2 (item (56) Other Publications), Lines 27-28, delete "Neurons."" and insert -- Neurons," --

Column 2 (item (56) Other Publications), Lines 32-33, delete "Taiwan."" and insert -- Taiwan," --

Signed and Sealed this  
Twenty-third Day of February, 2021

Drew Hirshfeld  
*Performing the Functions and Duties of the*  
*Under Secretary of Commerce for Intellectual Property and*  
*Director of the United States Patent and Trademark Office*